US012653959B2

(12) United States Patent
Kumar et al.

(10) Patent No.: US 12,653,959 B2
(45) Date of Patent: Jun. 16, 2026

(54) SINGLE-HAND REMOVABLE TIP CAP FOR PREFILLED SYRINGE

(71) Applicant: Becton, Dickinson and Company, Franklin Lakes, NJ (US)

(72) Inventors: Manish Kumar, Bengaluru (IN); Shishir Prasad, Ramsey, NJ (US); Praveen Nalawade, Belagavi (IN); Karthik MR, Bangalore (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 822 days.

(21) Appl. No.: 17/979,182

(22) Filed: Nov. 2, 2022

(65) Prior Publication Data

US 2024/0139424 A1 May 2, 2024

(51) Int. Cl.
*A61M 5/32* (2006.01)
*A61M 5/31* (2006.01)
*A61M 5/315* (2006.01)

(52) U.S. Cl.
CPC ........ *A61M 5/3204* (2013.01); *A61M 5/3134* (2013.01); *A61M 5/31591* (2013.01)

(58) Field of Classification Search
CPC .............. A61M 5/3204; A61M 5/3134; A61M 2005/3104
See application file for complete search history.

(56) References Cited

U.S. PATENT DOCUMENTS

| | | | |
|---|---|---|---|
| 5,496,288 A | 3/1996 | Sweeney | |
| 8,671,496 B2 | 3/2014 | Vaillancourt et al. | |
| 8,696,820 B2 | 4/2014 | Vaillancourt et al. | |
| 11,083,847 B2 | 8/2021 | Mahmoodian | |
| 11,344,715 B2 | 5/2022 | Erekovcanski et al. | |
| D965,777 S | 10/2022 | Marici et al. | |
| 2013/0035643 A1* | 2/2013 | Kawamura | A61M 39/20 604/192 |
| 2013/0079726 A1 | 3/2013 | Madin | |
| 2014/0025017 A1 | 1/2014 | Horita et al. | |
| 2017/0356582 A1 | 12/2017 | Pappalardo | |
| 2019/0231984 A1* | 8/2019 | Mahmoodian | A61M 5/3134 |
| 2020/0061297 A1 | 2/2020 | Kosinski et al. | |
| 2021/0008237 A1 | 1/2021 | Okman et al. | |
| 2021/0008283 A1 | 1/2021 | San Solo et al. | |
| 2021/0069419 A1* | 3/2021 | Pappalardo | A61M 5/31 |
| 2021/0187266 A1 | 6/2021 | Ryan | |
| 2022/0233836 A1 | 7/2022 | Leibowitz | |
| 2022/0273881 A1 | 9/2022 | Mahmoodian et al. | |

* cited by examiner

*Primary Examiner* — Bradley J Osinski

(74) *Attorney, Agent, or Firm* — Servilla Whitney LLC

(57) ABSTRACT

A syringe includes a barrel having a proximal end, a distal end having a distal tip defining a channel, and a sidewall extending between the proximal end and the distal end. The syringe also includes a tip cap removably connected to the distal tip of the barrel restricting fluid flow from the channel. The tip cap includes a connector configured to receive the distal tip of the barrel forming a friction engagement with the distal tip, a cap shield connected to and extending about the connector, and a release tab extending proximally from the cap shield that secures the tip cap to the barrel. A prefilled flushing syringe including a predetermined volume of a fluid disposed within the barred of the syringe, as well as methods for expulsion of fluid from the syringe and of assembling the syringe and tip cap are also disclosed herein.

18 Claims, 10 Drawing Sheets

OBTAIN PREFILLED SYRINGE CONTAINING VOLUME OF FLUID —210

REMOVE PACKAGING FROM PREFILLED SYRINGE —212

REMOVE TIP CAP FROM DISTAL END OF PREFILLED SYRINGE —214

ADVANCE STOPPER THROUGH BARREL TO PRIME SYRINGE —216

ATTACH DISTAL TIP OF SYRINGE TO VASCULAR ACCESS DEVICE —218

MOVE STOPPER THROUGH BARREL TO EXPEL FLUID FROM SYRINGE —220

DISCONNECT SYRINGE FROM VASCULAR ACCESS DEVICE —222

SLIDE COLLAR ONTO DISTAL SHIELD OF SYRINGE BARREL — 310

SLIDE DISTAL RING OF TETHER ONTO TIP CAP — 312

SLIDE TIP CAP OVER DISTAL TIP OF SYRINGE BARREL — 314

SINGLE-HAND REMOVABLE TIP CAP FOR PREFILLED SYRINGE

BACKGROUND OF THE INVENTION

Field of the Invention

The present disclosure relates generally to tip caps for syringes, such as prefilled syringes, and, in particular, to a tip cap, which can be easily removed from a distal tip of the syringe by a practitioner, preferably using one hand.

Description of Related Art

Conventional syringes comprise a barrel having an open proximal end and an opposed distal end. A distal tip, sometimes referred to as a luer or luer tip, projects from the distal end of the syringe barrel and includes a narrow passage or channel in fluid communication with an interior of the syringe barrel. Conventional syringes are often prefilled during manufacture with medical fluids, such as flush solutions or therapeutic agents. When prefilled with the medical fluid, the syringe barrel can be sealed to prevent contamination of the medical fluid or loss of the medical fluid prior to use. Seals also prevent practitioners from being needlessly exposed to the medical fluid contained in the syringe barrel, which can be particularly important for toxic or otherwise harmful medications.

Some prefilled syringes have stoppers or closures, often referred to as tip caps, mounted over the distal tip of the syringe barrel for sealing the syringe barrel to prevent leakage and to avoid contamination of the medical fluid contained therein. Conventional tip caps are removed from the distal tip of the syringe barrel by the practitioner shortly before using the syringe by grasping the syringe barrel and pulling the tip cap axially away from the syringe barrel. Other tip caps are attached to a syringe barrel by a threaded collar. In such instances, the tip cap can be removed from the syringe barrel by holding the syringe barrel with one hand, while twisting the tip cap with the other hand to unscrew the tip cap. When a prefilled syringe is capped with a tip cap, it is especially important that a good seal be maintained. This is usually achieved by tightly affixing the tip cap to the distal tip of the syringe barrel. However, when overly tightened, the tip cap can be difficult to remove or may be damaged. Further, a prefilled syringe may be autoclaved after filling and capping so that the prefilled syringe is contained within sterile packaging. The autoclaving procedure can cause interactions between the tip cap and the syringe barrel, which can further increase the difficulty in removing the tip cap from the distal tip of the syringe barrel.

Due to the tight connection between the tip cap and distal tip of the syringe barrel, the practitioner may be required to apply a substantial gripping force to remove the tip cap from the distal end of the syringe barrel. Tightly grasping the tip cap can be difficult for some practitioners who may lack physical strength and dexterity needed to correctly grip the tip cap, especially considering the small size of the typical tip cap. Further, when tightly grasping the tip cap, the practitioner's fingers are in close proximity to the distal tip of the syringe barrel. Accordingly, there is a risk that the practitioner will contact the distal tip of the barrel, while removing the tip cap, which can contaminate the distal tip of the syringe barrel.

Prefilled syringes are often connected to and used to deliver fluid to a patient through vascular access devices (VADs), such as intravenous (IV) catheters (e.g., peripheral catheters or central venous catheters). If not properly maintained or if exposed to non-sterile environments, which, as described previously, can occur as the practitioner manipulates or removes the tip cap from the syringe barrel, the VADs can become contaminated, sealed with blood clots, and/or can spread infection. Many medical facilities implement sterile practices and protocols to avoid contamination and to ensure that VADs are used properly and do not become sealed or infected. These protocols often include sterilizing medical devices including the VAD and flushing the catheter with a flush solution. Specifically, VAD standards of practice usually recommend flush procedures be performed after catheter placement, before fluid infusion, and before and after drug administration, blood sampling, transfusions, and/or administration of parenteral nutrition. These flush procedures are intended to confirm catheter patency, avoid drug incompatibilities, ensure that the complete drug dose is administered to the patient, prevent thrombus formation, and minimize a risk of bloodstream infections caused by contamination of the VAD.

While sterilization procedures implemented by medical facilities certainly address some contamination risks, improved designs for medical devices and tools that reduce opportunities for contamination and simplify device use are needed. In particular, syringe designs that ensure that the distal tip of the syringe barrel remains sterile and free from contamination throughout a fluid delivery procedure using the VAD will address many current contamination problems that arise during an infusion procedure. Further, syringe and tip cap designs that are easy to open or remove and which can be manipulated without touching the syringe distal tip will reduce common contamination risks for conventional prefilled syringes. The syringe and tip cap designs of the present disclosure addresses these issues.

SUMMARY OF THE INVENTION

According to an aspect of the disclosure, a syringe includes a barrel having a proximal end, a distal end comprising a distal tip defining a channel, and a sidewall extending between the proximal end and the distal end. The syringe also includes a tip cap removably connected to the distal tip of the barrel restricting fluid flow from the channel. The tip cap includes a connector configured to receive the distal tip of the barrel forming a friction engagement with the distal tip, a cap shield connected to and extending about the connector, and a release tab extending proximally from the cap shield that secures the tip cap to the barrel.

According to another aspect of the disclosure, a prefilled flushing syringe includes the previously described syringe and a predetermined volume of a fluid disposed in the barrel of the prefilled syringe. The prefilled syringe is configured such that the distal tip of the barrel is received within the connector of the tip cap, thereby preventing the fluid in the barrel from passing through the channel to a distal opening of the barrel. Also, the release tab of the tip cap is engaged to a portion of the barrel, thereby securing the tip cap to the barrel.

According to another aspect of the disclosure, a method for expulsion of fluid from the syringe, as previously described, includes: removing the tip cap from the distal tip of the syringe barrel; attaching the distal tip of the syringe barrel to a vascular access device; and moving a plunger inserted in the barrel of the syringe through the barrel to expel the fluid from the barrel and through the channel of the distal tip of the barrel to the vascular access device.

According to another aspect of the disclosure, a method for assembly of the previously described syringe includes: attaching a collar over a distal shield of the syringe barrel; attaching a distal ring of a tether over the tip cap; and moving the connector of the tip cap over the distal tip of the barrel, thereby forming an assembled syringe.

In accordance with an embodiment of the present invention, a syringe includes a barrel having a proximal end, a distal end having a distal tip defining a channel, and a sidewall extending between the proximal end and the distal end, and a tip cap removably connected to the distal tip of the barrel restricting fluid flow from the channel. The tip cap including a connector configured to receive the distal tip of the barrel forming a friction engagement with the distal tip, a cap shield connected to and extending about the connector, and a release tab extending proximally from the cap shield that secures the tip cap to the barrel.

In accordance with an embodiment of the present invention, the barrel includes at least one of polyester, polycarbonate, polypropylene, polyethylene, polyethylene tereph-thalate, or acrylonitrile butadiene styrene.

In accordance with an embodiment of the present invention, the barrel further includes an annular flange about the proximal end of the barrel for grasping the barrel and a plunger that moves through the barrel.

In accordance with an embodiment of the present invention, the sidewall of the barrel includes a tapered portion between the distal end of the barrel and other portions of the barrel for guiding fluid in the barrel towards the channel of the distal tip.

In accordance with an embodiment of the present invention, the distal tip includes a frusto-conical tip that forms a slip engagement with an inner surface of the connector of the tip cap.

In accordance with an embodiment of the present invention, the distal tip includes a male luer connector.

In accordance with an embodiment of the present invention, the channel extends from an interior of the barrel to a distal opening of the distal tip.

In accordance with an embodiment of the present invention, a tether connects the barrel to the tip cap so that the tip cap hangs from the barrel when the connector of the tip cap is removed from the distal tip of the barrel.

In accordance with an embodiment of the present invention, the distal end of the barrel further includes a distal shield at least partially enclosing the distal tip of the barrel.

In accordance with an embodiment of the present invention, distal shield of the barrel includes a proximal end connected to the syringe barrel, an open distal end, and a sidewall extending between the proximal end and the distal end of the distal shield.

In accordance with an embodiment of the present invention, the distal shield of the barrel includes an inner surface comprising threads for connecting the barrel to a threaded female luer connector.

In accordance with an embodiment of the present invention, a collar is provided around the distal shield of the barrel, and wherein the release tab comprises a catch removably engaged to the collar.

In accordance with an embodiment of the present invention, the collar is engaged about an outer surface of the distal shield of the barrel.

In accordance with an embodiment of the present invention, the collar includes a plastic ring.

In accordance with an embodiment of the present invention, a tether connecting the barrel to the tip cap so that the tip cap can hang from the barrel when the connector of the tip cap is removed from the distal tip of the barrel, and wherein the tether includes a proximal ring positioned about the distal shield of the barrel, a distal ring connected about the cap shield of the tip cap, and a connecting member extending between the proximal ring and the distal ring.

In accordance with an embodiment of the present invention, the connecting member is flexible.

In accordance with an embodiment of the present invention, the proximal ring, the distal ring, and the connecting member includes a flexible elastomeric material.

In accordance with an embodiment of the present invention, a plunger is positioned in the barrel for expelling fluid from the barrel through the channel of the distal tip.

In accordance with an embodiment of the present invention, the syringe is capable of single-hand operation, both to remove the tip cap from the distal opening of the barrel and to expel fluid from the barrel through the channel of the barrel by moving the plunger through the barrel.

In accordance with an embodiment of the present invention, the plunger includes a stopper positioned in the barrel and a plunger rod extending proximally from the stopper through the proximal end portion of the barrel.

In accordance with an embodiment of the present invention, the stopper includes a thermoplastic elastomer, such as isoprene.

In accordance with an embodiment of the present invention, the stopper includes a proximal end, a distal end, and an outer surface extending between the proximal end and the distal end that seals against an inner surface of the barrel.

In accordance with an embodiment of the present invention, the plunger rod includes a connector portion inserted into and engaged to a cavity of the stopper for securing the stopper to the plunger rod.

In accordance with an embodiment of the present invention, the connector of the tip cap defines a frusto-conical cavity sized to receive the distal tip of the barrel.

In accordance with an embodiment of the present invention, the connector of the tip cap includes a female luer connector sized to receive the distal tip of the barrel.

In accordance with an embodiment of the present invention, the connector of the tip cap is tapered, such that an inner diameter of a proximal end of the connector is wider than an inner diameter of a distal tip of the connector.

In accordance with an embodiment of the present invention, the outer surface of the connector of the tip cap does not include threads.

In accordance with an embodiment of the present invention, the cap shield of the tip cap includes a proximal end comprising a flange connected to and extending radially from the connector of the tip cap, an open distal end, and a sidewall extending between the proximal end and the distal end.

In accordance with an embodiment of the present invention, the sidewall of the cap shield includes a plurality of protrusions, such as ribs, ridges, or detents, extending outwardly from an outer surface of the cap shield.

In accordance with an embodiment of the present invention, a stem extends distally from a distal end of the connector and enclosed by the cap shield of the tip cap.

In accordance with an embodiment of the present invention, the release tab includes a proximal end having a catch for engaging the barrel, a distal end pivotally connected to the cap shield of the tip cap, and a beam extending between the proximal end and the distal end.

In accordance with an embodiment of the present invention, the proximal end of the release tab further includes a push surface positioned transverse or substantially transverse to a longitudinal axis of the connector of the tip cap and to a longitudinal axis of the cap shield of the tip cap.

In accordance with an embodiment of the present invention, wherein pressing on the push surface causes the beam to pivot about the distal end of the release tab, which releases the catch from the barrel, and wherein continuing to press against the push surface overcomes the friction engagement between the connector of the tip cap and the distal tip of the barrel, which disconnects the tip cap from the distal tip of the barrel.

In accordance with an embodiment of the present invention, a prefilled flushing syringe having a predetermined volume of a fluid disposed in the barrel of the prefilled syringe, wherein the distal tip of the barrel is received within the connector of the tip cap, thereby preventing the fluid in the barrel from passing through the channel to a distal opening of the barrel, and wherein the release tab of the tip cap is engaged to a portion of the barrel, thereby securing the tip cap to the barrel.

In accordance with an embodiment of the present invention, the fluid includes a saline flush solution.

In accordance with an embodiment of the present invention, the fluid includes a therapeutic agent.

In accordance with an embodiment of the present invention, the barrel contains from about 1 mL to about 50 mL of the fluid.

In accordance with an embodiment of the present invention, the syringe further includes a collar connected about a distal shield of the syringe, and wherein the release tab includes a catch engaged to the collar.

In accordance with an embodiment of the present invention, a method for expulsion of fluid from a syringe includes removing the tip cap from the distal tip of the syringe barrel, attaching the distal tip of the syringe barrel to a vascular access device, and moving a plunger inserted in the barrel through the barrel to expel the fluid from the barrel and through the channel of the distal tip of the barrel to the vascular access device.

In accordance with an embodiment of the present invention, the fluid contained in the barrel of the syringe includes a saline flush solution.

In accordance with an embodiment of the present invention, the fluid contained in the barrel of the syringe includes a therapeutic agent.

In accordance with an embodiment of the present invention, the barrel contains from about 1 mL to about 50 mL of the fluid.

In accordance with an embodiment of the present invention, wherein removing the tip cap from the distal tip of the barrel includes pressing the release tab to disengage the release tab from the barrel and, once the release tab is disengaged, continuing to apply axial force to the release tap to overcome the friction engagement between the connector of the tip cap and the distal tip of the barrel.

In accordance with an embodiment of the present invention, wherein the tip cap is manually removed from the barrel with one hand.

In accordance with an embodiment of the present invention, advancing the plunger through the barrel by a small amount prior to attaching the syringe to the VAD removes air from an interior of the barrel.

In accordance with an embodiment of the present invention, wherein attaching the syringe barrel to the VAD comprises inserting the distal tip of the syringe barrel through a septum of a fluid port of the VAD and twisting the syringe, such that threads of the syringe engage corresponding threads of a female connector of the VAD.

In accordance with an embodiment of the present invention, wherein the distal tip of the barrel includes a male luer connector, which is attached to a female luer connector of the VAD by inserting the male luer connector into the female luer connector.

In accordance with an embodiment of the present invention, including attaching a collar over a distal shield of the syringe barrel; attaching a distal ring of a tether onto the tip cap, and moving the connector of the tip cap over the distal tip of the barrel, thereby forming an assembled syringe.

In accordance with an embodiment of the present invention, wherein attaching the collar to the distal shield includes sliding the collar onto the distal shield, such that the collar is retained on the distal shield by a friction engagement.

In accordance with an embodiment of the present invention, wherein the tether includes a proximal ring, the distal ring, and a flexible connector extending between the proximal ring and the distal ring.

In accordance with an embodiment of the present invention, including sliding the proximal ring of the tether onto the distal shield of the syringe barrel.

In accordance with an embodiment of the present invention, including moving the connector of the tip cap over the distal tip of the barrel causes the release tab to form an interference engagement with the collar.

DESCRIPTION OF THE INVENTION

Figure 1A:
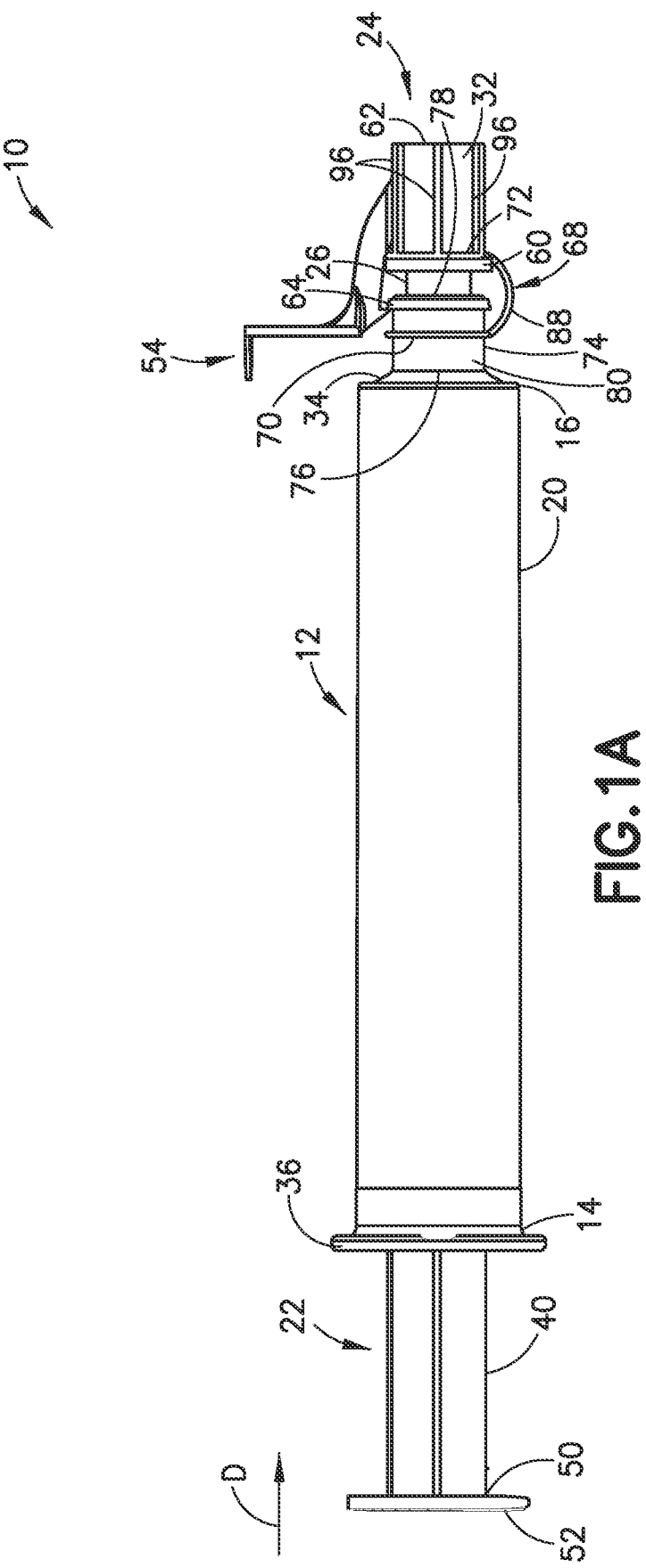
FIG. 1A is a front view of a tip cap mounted to a syringe, according to an aspect of the present disclosure.
Figure 1B:
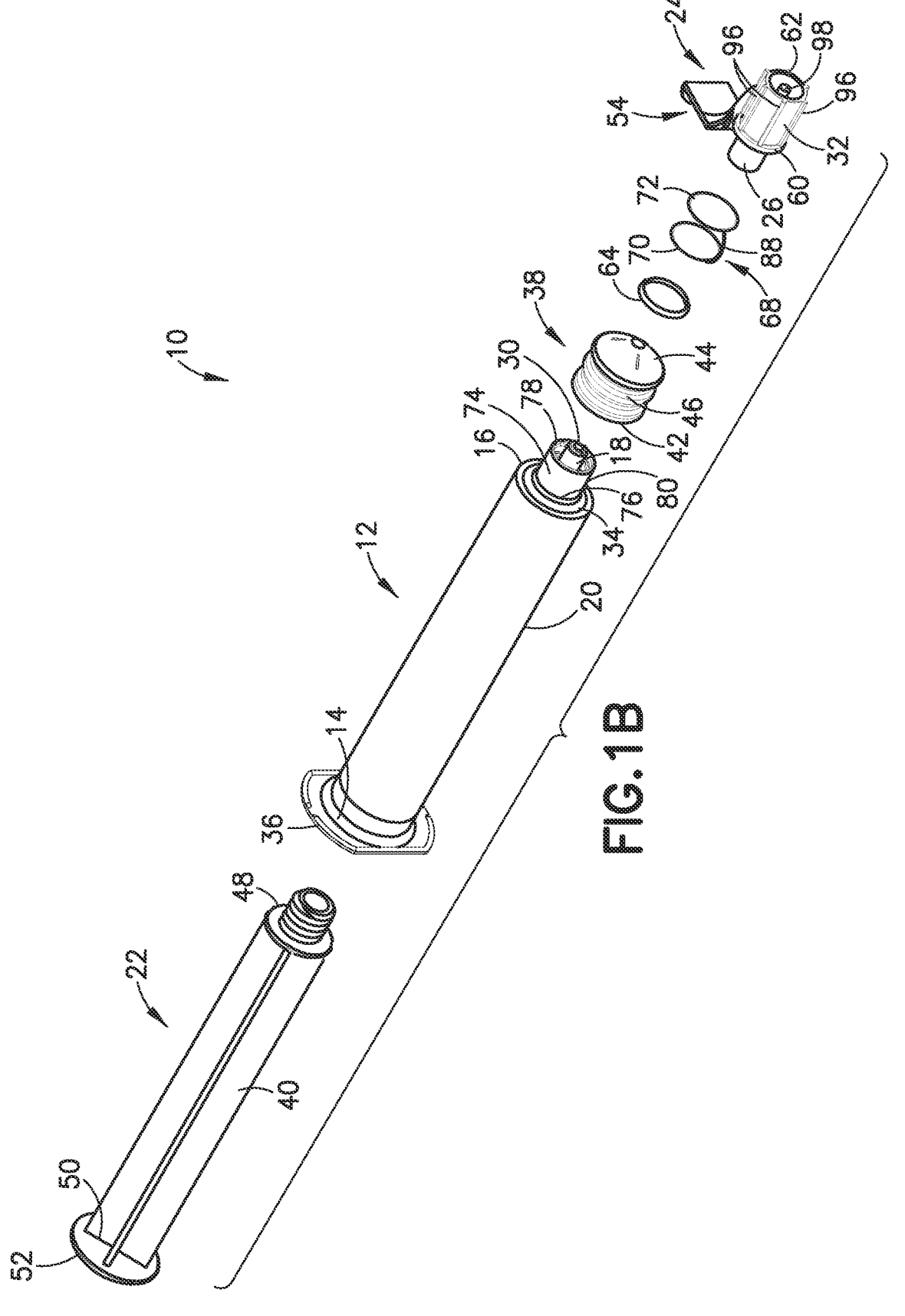
FIG. 1B is an exploded view of the tip cap and syringe of FIG. 1A.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. As used herein, the term "proximal" refers to a portion or end of a device, such as a syringe or catheter, which is grasped, manipulated, or used by a practitioner or another user. The term "distal" refers to an end or portion of the device that is farthest away from the portion of the device that is grasped, manipulated, or used by the practitioner. For example, the "proximal end" of a catheter or IV line refers to the end including a fluid port that is connected to a fluid container, such as an IV bag or syringe. The "distal end" of the catheter or IV line refers to the end that is connected to the patient. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

With reference to the figures, the present disclosure is directed to syringes 10, such as prefilled syringes, having a distal tip covered by a tip cap 24 and configured to be used by a practitioner for delivering a medical fluid to a patient through, for example, a vascular access device (VAD). The practitioner can be, for example, a medical technician, nurse, physician assistant, physician, or other trained or untrained clinicians or medical caregivers. The medical fluid can be a flush solution, such as saline and/or a heparin lock flush solution. An example of a saline flush solution is 0.9% sodium chloride USP for injection. An example of a heparin lock flush solution is 0.9% sodium chloride with 100 USP units of heparin sodium per mL or 10 USP units of heparin sodium per mL. Other flush solutions, as are known in the art, can also be used with the syringes 10 of the present disclosure. The medical fluid can also be a medication, a total parenteral nutrient (TPN) liquid, or another therapeutic agent used for treatment of chronic or acute conditions. Exemplary therapeutic agents can include, for example, drugs, chemicals, biological or biochemical substances that, when delivered in a therapeutically effective amount to the patient, achieve a desired therapeutic effect.

The syringes 10 and tip caps 24 of the present disclosure are intended to reduce contamination risks and to ensure that the distal tip of the syringe remains sterile and free from contamination prior to and while it is connected to the VAD. Further, the syringes 10 of the present disclosure are designed for easy operation and, in particular, to avoid difficulties with removing tip caps of conventional prefilled syringes and caps. In some particularly advantageous examples, the syringes 10 and tip caps 24 of the present disclosure can be operated by a practitioner with one hand. Further, the syringes 10 and tip caps 24 can be configured so that practitioner touches only proximal portions of the tip cap 24, making it less likely that a practitioner will touch or contaminate distal portions of the syringe 10 while removing the tip cap 24. Specifically, the practitioner desirably should be able to remove the tip cap 24 from the syringe 10 with one hand by manipulating a tab of a tip cap 24 to release the tip cap 24 from the syringe 10. By contrast, for conventional prefilled syringes, a practitioner may need to grasp a syringe barrel of the syringe 10 with one hand and grasp the tip cap 24 with the other hand in order to pull a tightly fitted tip cap 24 away from the distal tip of the syringe barrel. Once the tip cap 24 is disconnected or removed, the practitioner is able to expel the medical fluid from the syringe barrel of the syringe 10 with one hand by, for example, pushing a plunger or stopper through the syringe barrel.

In some examples, the syringes 10 disclosed herein include tethers or other flexible retainers for holding the tip cap 24 in proximity to the distal end or the syringe 10 even after the tip cap 24 is otherwise disconnected from the distal tip of the syringe 10. In particular, the tether or another flexible connector can be configured such that when the tip cap 24 is removed from the syringe 10, the tip cap 24 hangs from the tether or another connector in proximity of a distal end of the syringe 10. Securing the tip cap 24 to the syringe 10 through the tether ensures that the tip cap 24 does not become a hazard or obstruction preventing the practitioner from using the syringe 10 in an expected manner. For example, because the tip cap 24 is connected to the syringe barrel through the tether, the tip cap 24 does not become a choking hazard, as occurs with other small single-use or discardable molded parts. Also, the tether prevents the tip cap 24 from falling off the syringe 10 and landing in inconvenient locations of, for example, a medical facility or surgical site, as may occur for other caps, clips, or syringe accessories that are not connected to the syringe barrel by a tether or connector.

In some examples, the tip caps 24 of the present disclosure can be configured to be connected to conventional prefilled syringes, such as to a prefilled syringe that includes a male needleless connector or male luer connector at a distal end thereof. For example, as described in further detail herein, a collar or another anchoring device can be attached to the distal end of the conventional prefilled syringe. The tip cap 24 can be engaged to the distal end of the syringe through the collar or anchoring device, which secures the tip cap 24 to the syringe 10. In other examples, the syringe 10 can be specifically designed, molded, or configured to use with the tip caps 24 disclosed herein. For example, the syringe can include an integrally molded collar or anchor that engages the tip cap 24 for securing the tip cap 24 to the syringe 10.

In some examples, the syringes 10 of the present disclosure can be provided as prefilled syringes capped by the tip cap 24 and containing the flush solution or other medical fluid. The prefilled syringes 10 can also include clips, retainers, and/or other packaging to hold the plunger rod in place and to ensure that the flush solution or another medical fluid does not leak from the prefilled syringe 10 at unexpected times, such as during transport.

Prefilled Syringes and Tip Caps

With reference to FIGS. 1A-3C, in some examples, the syringe 10 of the present disclosure comprises a barrel 12, which can comprise a proximal end 14, a distal end 16 comprising a distal tip 18 defining a channel 28 for expelling fluid, such as a medical fluid F (shown in FIGS. 2A-2C), from an interior of the barrel 12, and a sidewall 20 extending between the proximal end 14 and the distal end 16. The channel 28 can extend, for example, through the distal tip 18 from the interior of the barrel 12 to a distal opening 30. The syringe 10 can further comprise a plunger 22 (shown in FIGS. 1A and 1B) positioned in the barrel 12 for expelling the medical fluid F (shown in FIGS. 2A-2C) from the barrel 12 through the channel 28 of the distal tip 18.

The syringe 10 further comprises the tip cap 24 removably connected to the distal end 16 of the barrel 12 for sealing the medical fluid F within the barrel 12 and/or for restricting fluid flow from the channel 28 of the barrel 12. The tip cap 24 can comprise a connector 26 configured to receive the distal tip 18 of the barrel 12 forming a friction engagement with the distal tip 18, a cap shield 32 connected to and extending about the connector 26, and a release tab 54 extending proximally from the cap shield 32 that secures the tip cap 24 to the barrel 12.

As used herein, a "friction engagement" can refer to a connection between a surface of a first part, such as an inner surface of the connector 26 of the tip cap 24, and a surface of a second part, such as an outer surface of the distal tip 18. To form the friction engagement, the surfaces are in face-to-face contact such that friction prevents or restricts the surfaces from sliding away from one another. Accordingly, the surfaces can be free from protrusions, grooves, ridges, ribs, detents, or other locking structures necessary for forming other types of engagements between the first part and the second part. Also, mechanical fasteners or adhesives may not be needed for securing the first part to the second part. Instead, the friction between the surfaces can be sufficient to restrict movement of the first part relative to the second part. The friction engagement can be overcome by applying sufficient force to the first part and/or to the second part so that the surfaces slide away from one another overcoming the frictional forces between the two surfaces.

In some examples, the tip cap 24 is configured to be manually removable, meaning that the practitioner can grasp a portion of the tip cap 24 and manipulate portions of the tip cap 24 to manually remove the tip cap 24 from the barrel 12. Further, the tip cap 24 can be configured for single-hand operation. In particular, the practitioner desirably is able both to remove the tip cap 24 from the barrel 12 and move the plunger 22 through the barrel using one hand to expel the medical fluid F from the barrel 12 through the channel 28 of the distal tip 18. The tip cap 24 further comprises the cap shield 32 extending about the connector 26. The cap shield 32 can be an annular or tubular structure having a proximal end 60 connected to a proximal end of the connector 26 and an open distal end 62 that encloses or surrounds the connector 26.

With continued reference to FIGS. 1A-3C, in some examples, the distal tip 18 of the barrel 12 can be an elongated and/or tubular member defining the channel 28, which extends from a tapered portion 34 of the barrel 12 to the distal opening 30 of the distal tip 18. In some examples, the distal tip 18 can be a frusto-conical member or structure, which can be sized to form the friction or slip-type engagement with an inner surface 56 of the connector 26 of the tip cap 24. In some examples, the distal tip 18 can be a male needleless connector or male luer connector that is configured to be inserted into the connector 26 and also into a female needless connector, such as a fluid port or opening of a VAD.

As used herein, a "luer connector" refers to a connector that includes a tapered portion (i.e., a luer taper) for creating the friction engagement between the distal tip 18 and a tapered cavity, such as a cavity of a female luer connector, configured to receive and engage the distal tip 18. Accordingly, the distal tip 18 of the present disclosure can be a tapered elongated structure where an outer diameter of a proximal end of the distal tip 18 is wider than an outer diameter of a distal end of the distal tip 18. Similarly, an inner diameter of a proximal end of the connector 26 can be wider than an inner diameter of a distal end of the connector 26, so that the tapered distal tip 18 can be received in the connector 26.

As previously described, the distal tip 18 of the barrel 12 can be configured to be connected directly or indirectly to a female connector, which forms a fluid port, valve, or another terminal access portion of the VAD. In particular, a common type of fluid port of a VAD is a pierceable septum or pre-slit septum made of rubber or another elastomeric material. The septum can be pierced or opened by a blunt elongated member or a frusto-conically shaped tip, such as the distal tip 18 of the barrel 12, in order to provide fluid communication between the interior of the barrel 12 and the VAD for infusing fluids to or withdrawing fluids from a catheter of the VAD. More specifically, in some examples, the distal tip 18 can be configured to be used with female needleless connectors, specifically female luer connectors for a range of dimensions permitted by various design protocols, such as ISO 80369-7:2016 or ISO 80369-7:2021 (Female Luer Lock Connector dimensions).

In some examples, the barrel 12 of the syringe 10 can be a conventional fluid-delivery syringe barrel used for medical procedures made by, for example, an injection molding process. For example, the barrel 12 can be substantially similar or identical in shape, size, and configuration to barrels of syringes used for administering a flush solution to a VAD, as are known in the art. In some examples, the barrel 12 can be a cylindrical or elliptical prism structure formed from a rigid thermoplastic material, such as polyester, polycarbonate, polypropylene, polyethylene, polyethylene terephthalate, acrylonitrile butadiene styrene, or other injection moldable or formable resin materials, as are known in the art. Exemplary barrels 12 for flush syringes are described, for example, in U.S. Patent Appl. Pub. No. 2020/0061297, entitled "Flush Syringe Assembly with Controlled Pulsatile Flushing," which is incorporated herein by reference in its entirety. Dimensions of the syringe barrel 12 can be determined based on the type of fluid injection being performed. For example, the barrel 12 can define an interior that contains about 1 mL to about 50 ml of the medical fluid F or, preferably from about 5 mL to 20 mL of the medical fluid F.

In some examples, the sidewall 20 of the barrel 12 comprises the tapered portion 34 (shown in FIGS. 2A-2C) proximate to the distal end 16 of the barrel 12. The tapered portion 34 can be positioned between the distal tip 18 of the barrel 12 and other portions of the sidewall 20 of the barrel 12. The tapered portion 34 can be configured to guide fluid in the barrel 12 towards the channel 28 of the distal tip 18 for expelling the medical fluid F in the barrel 12 through the distal opening 30 of the distal tip 18. In some examples, the tapered portion 34 can be shaped to reduce dead space having a sloped or angled surface corresponding with a distal surface of a stopper or plunger 22, which moves through the interior of the barrel 12, to ensure that the fluid moves through the barrel 12 to the channel 28. Reducing or eliminating dead space between the stopper or plunger 22 and the distal end 16 of the barrel 12 helps to ensure that the appropriate or expected amount of fluid is expelled from the barrel 12. In some examples, the barrel 12 further comprises a finger flange 36 or grip. The finger flange 36 can extend about the proximal end 14 of the barrel 12 for grasping the barrel 12 and plunger 22 to move the plunger 22 through the barrel 12.

The barrel 12 can further comprise a distal shield 74 on the distal end 16 of the barrel 12. The distal shield 74 can be a tubular structure that at least partially encloses the distal tip 18 of the barrel 12. The distal shield 74 of the barrel 12 can comprise a proximal end 76 connected to the syringe barrel 12, an open distal end 78, and a sidewall 80 extending between the proximal end 76 and the distal end 78 of the distal shield 74. Further, the distal shield 74 of the barrel 12 can comprise an inner surface 84 comprising threads 86 for connecting the barrel 12 to a threaded female luer connector. In some examples, the threads 86 of the distal shield 74 can be configured to mate to female connector threads with a width at a crest of each thread of from about 0.3 mm to about 1.0 mm and a width at a root of the thread from about 0.5 mm to about 1.2 mm. The distal tip 18 or end of the syringe barrel 12 can extend distally beyond the open distal end 78 of the distal shield 74, such that the distal tip 18 can be inserted through a cover or septum over an opening or fluid port of the female connector.

In some examples, the syringe 10 further comprises a collar 64 around the distal shield 74 of the barrel 12. For example, the collar 64 can be engaged about an outer surface of the distal shield 74 of the barrel 12 by a friction engagement. As described in further detail herein, the release tab 54 of the tip cap 24 can comprise a catch 112 removably engaged to the collar 64 for securing the tip cap 24 to the barrel 12. In some examples, the collar 64 can be a ring formed from a rigid plastic or flexible elastomeric material that slides over the distal shield 74 of the barrel 12. As previously described, the collar 64 can be configured to be used with a conventional prefilled syringe having a conventional distal tip 18 and distal shield 74. In such cases, the collar 64 can be a plastic or elastomeric ring that slides onto the distal shield 74 during assembly of the syringe 10 so that the tip cap 24 can be engaged to the syringe barrel 12. In other examples, the barrel 12 can be specifically molded for use with the tip cap 24 of the present disclosure. For example, the collar 64 or ring can be a protrusion, such as a ridge or rib, which is integrally formed with and extends radially outwardly from other portions of the distal shield 74. In such cases, the tip cap 24 can be engaged to the integral collar 64 or ring for securing the tip cap 24 to the barrel 12.

In some examples, the syringe 10 further comprises a tether 68 connecting the barrel 12 to the tip cap 24. The tether 68 can be configured to allow the tip cap 24 to hang from the barrel 12 when the connector 26 of the tip cap 24 is not connected to the distal tip 18 of the barrel 12. Instead, the tip cap 24 can hang freely from the barrel 12 a short distance away from the distal tip 18. Desirably, portions of the tether 68 are flexible, stretchable, and/or bendable so that the tip cap 24 can be easily moved away from the distal tip 18 and does not become an obstruction during use of the syringe 10. In particular, the practitioner should be able to move the tether 68 and tip cap 54 away from the distal tip 18 of the syringe 10 when attempting to insert the distal tip 18 of the syringe 10 into a fluid port or female connector of a VAD to perform a medical procedure.

In some examples, the tether 68 comprises a proximal ring 70 connected about the distal shield 74 of the barrel 12, a distal ring 72 connected about the cap shield 32 of the tip cap 24, and a connecting member 88 extending between the proximal ring 70 and the distal ring 72. The connecting member 88 can be a flexible, bendable, and/or stretchable member so that the tip cap 24 can be moved out of the way when using the syringe 10. In some examples, the proximal ring 70, the distal ring 72, and the connecting member 88 can be integrally formed as a single molded part. For example, the proximal ring 70, the distal ring 72, and the connecting member 88 of the tether 68 can be molded together from, for example, an elastomeric material, such as isoprene or silicone. In other examples, the connecting member 88 can be a separate part, such as an elastomeric segment, wire, or cord, connected to the proximal ring 70 and the distal ring 72 by a fastener, connector, or adhesive.

With reference again to FIGS. 1A and 1B, the syringe 10 further comprises the plunger 22 configured to move through an interior of the syringe barrel 12 for aspirating the medical fluid F into the interior of the syringe barrel 12 (if the syringe 10 is not a prefilled syringe 10) and/or for expelling the medical fluid F from the barrel 12 through the channel 28. In particular, the syringe 10 desirably is capable of single-hand operation, both to remove the tip cap 24 from the distal tip 18 of the barrel 12 and to expel medical fluid F from the barrel 12 through the channel 28 of the barrel 12 by moving the plunger 22 through the barrel 12.

In some examples, the plunger 22 comprises a stopper 38 and a plunger rod 40 connected to and extending from the stopper 38 and through the proximal end 14 of the barrel 12. The stopper 38 can have many features of conventional syringe stoppers or plungers, as are known in the art. For example, the stopper 38 can comprise a thermoplastic elastomer material, such as polypropylene or polyethylene, as well as from synthetic or natural rubber (e.g., isoprene). Further, the stopper 38 can comprise a proximal surface 42 or proximal end, a distal surface 44 or end, and an outer peripheral surface 46 extending between the proximal surface 42 and the distal surface 44. The outer peripheral surface 46 can be configured to seal against an inner surface of the sidewall 20 of the barrel 12 for moving the medical fluid F through the barrel 12. In some examples, the distal end or distal surface 44 of the stopper 38 can be tapered having a slope or angle that matches the tapered portion 34 of the sidewall 20 of the barrel 12, as previously described.

The plunger 22 also includes the plunger rod 40 connected to the stopper 38. The plunger rod 40 can be, for example, an injection molded part formed from a rigid thermoplastic material, such as polyester, polycarbonate, polypropylene, polyethylene, polyethylene terephthalate, or another thermoplastic material. The plunger rod 40 can include a distal end 48 engaged to the stopper 38. For example, the distal end 48 of the plunger rod 40 can include a connector that is inserted into a corresponding cavity or slot on the proximal surface 42 of the stopper 38. The plunger rod 40 can also include a proximal end 50 protruding proximally through the proximal end 14 of the barrel 12 and a body extending between the proximal end 50 and the distal end 48 of the plunger rod 40. The proximal end 50 of the plunger rod 40 can include a thumb press plate 52 for manipulating the plunger rod 40 to move the plunger rod 40 and stopper 38 through the syringe barrel 12. The body of the plunger rod 40 can have a variety of cross-sectional shapes and configurations within the scope of the present disclosure. For example, the body can have a generally cross shaped cross-section. In other examples, the cross-section of the plunger rod 40 can be an I-beam shape, hollow circle, hollow square, hollow rectangle, or L-shaped.

Figure 2A:
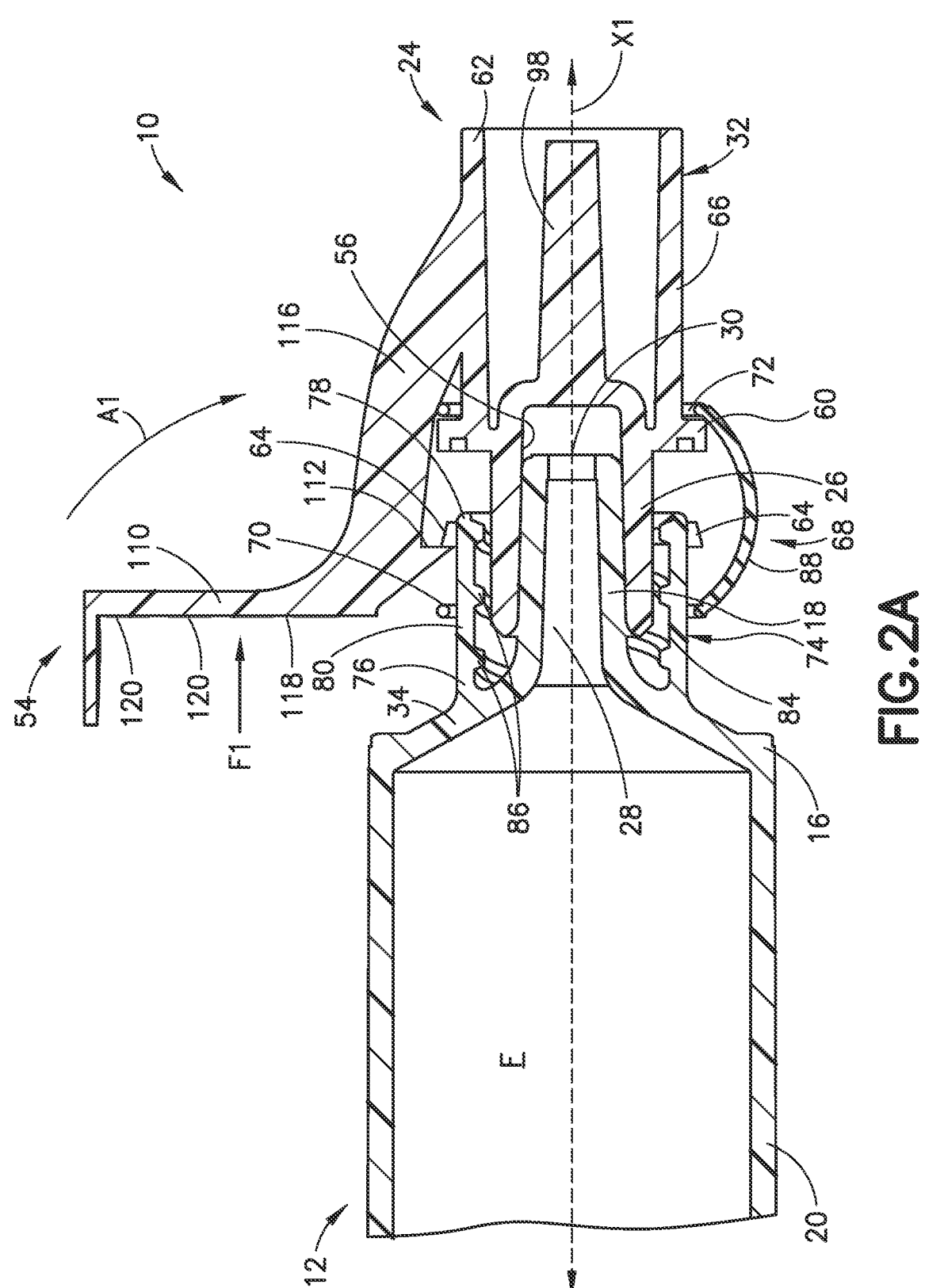
FIG. 2A is a cross-sectional view of the tip cap mounted to the syringe of FIG. 1A.
Figure 2B:
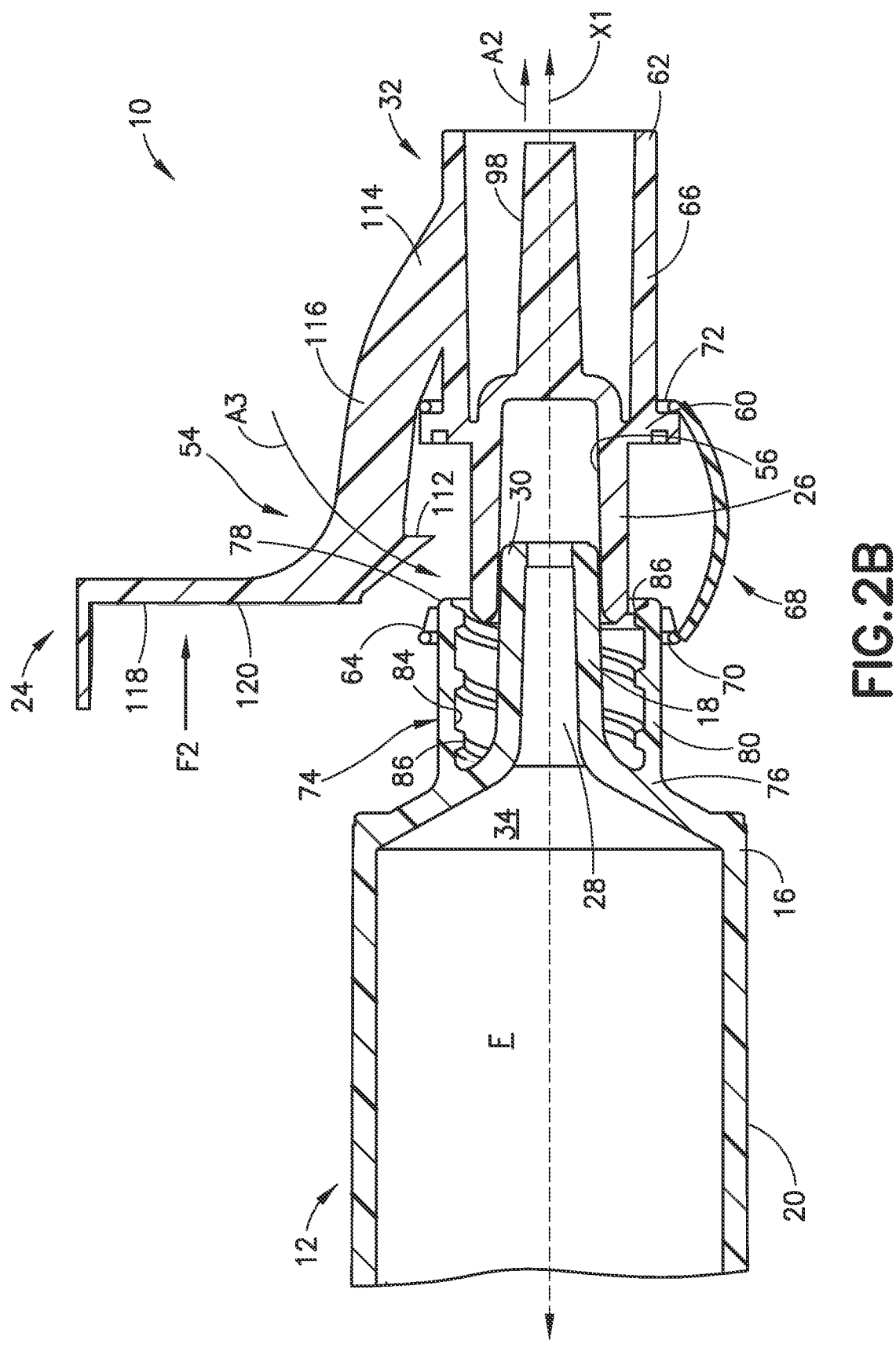
FIG. 2B is a cross-sectional view showing the tip cap partially removed from the syringe of FIG. 1A, according to an aspect of the disclosure.
Figure 2C:
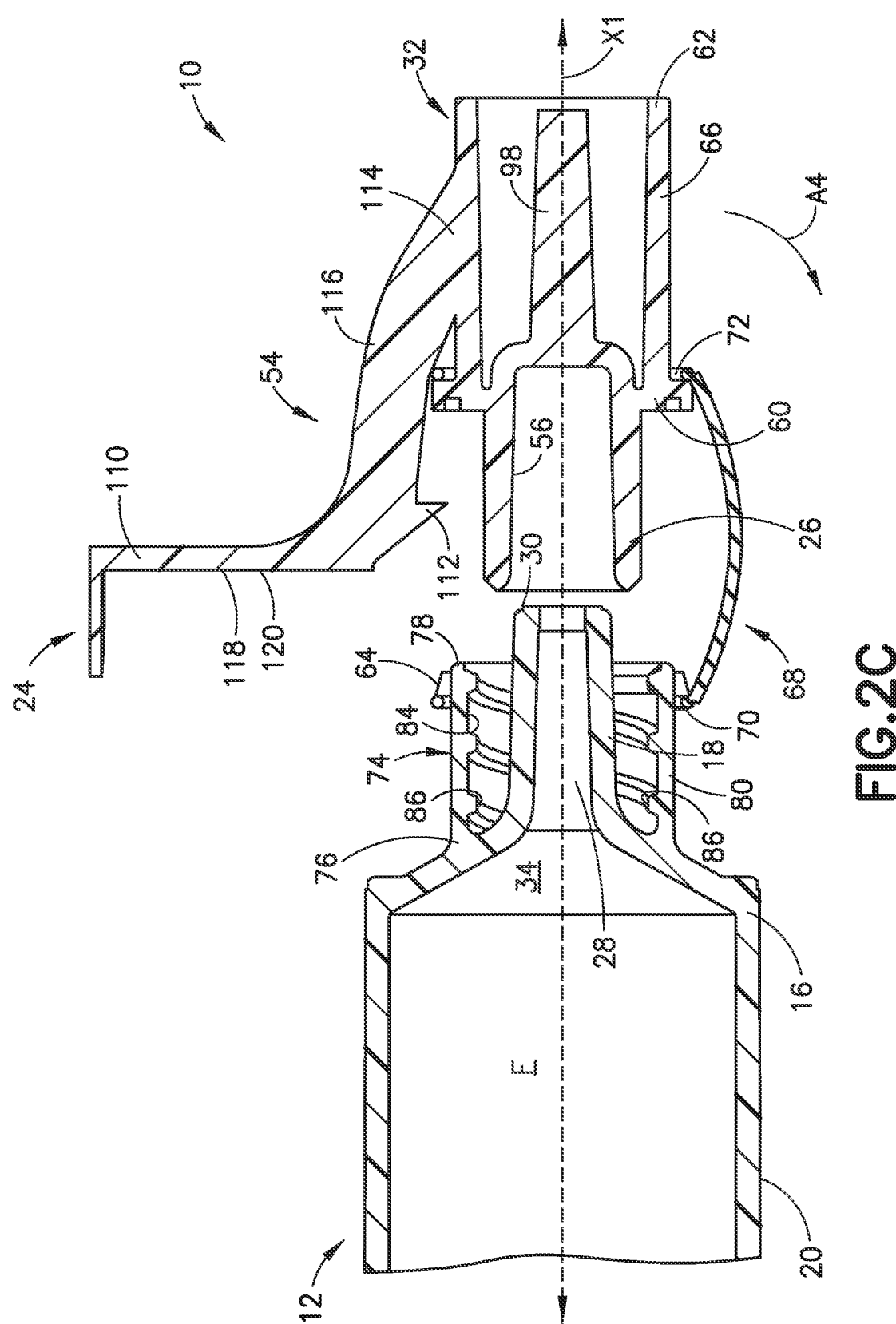
FIG. 2C is a cross-sectional view of the tip cap removed from the syringe of FIG. 1A, according to an aspect of the disclosure.
Figure 4B:
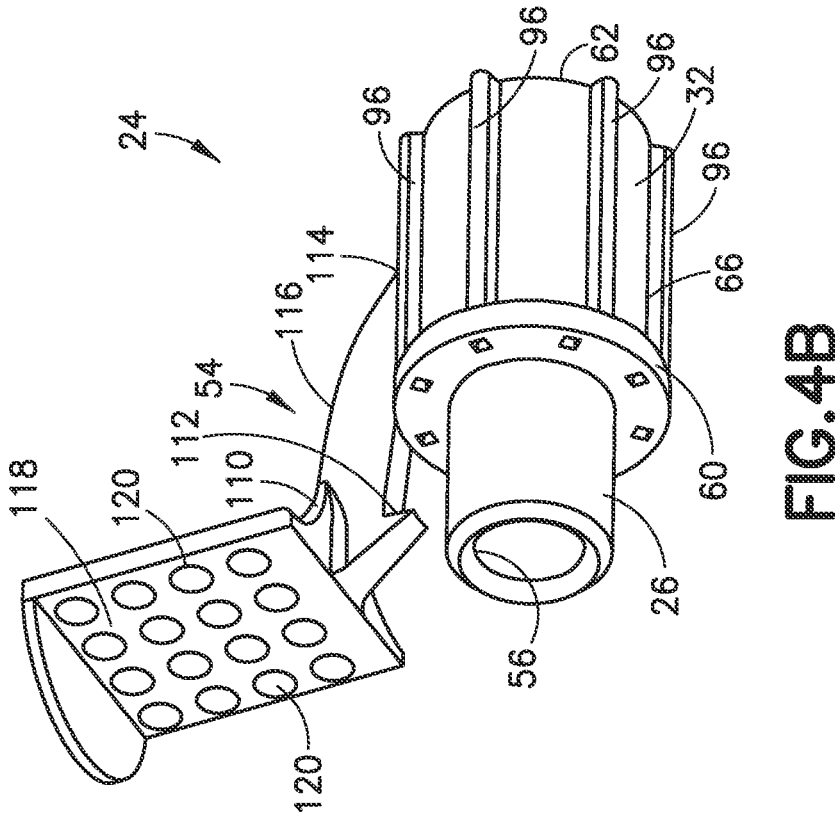
FIG. 4B is a perspective view of the tip cap of FIG. 1A, according to an aspect of the present disclosure.
Figure 4A:
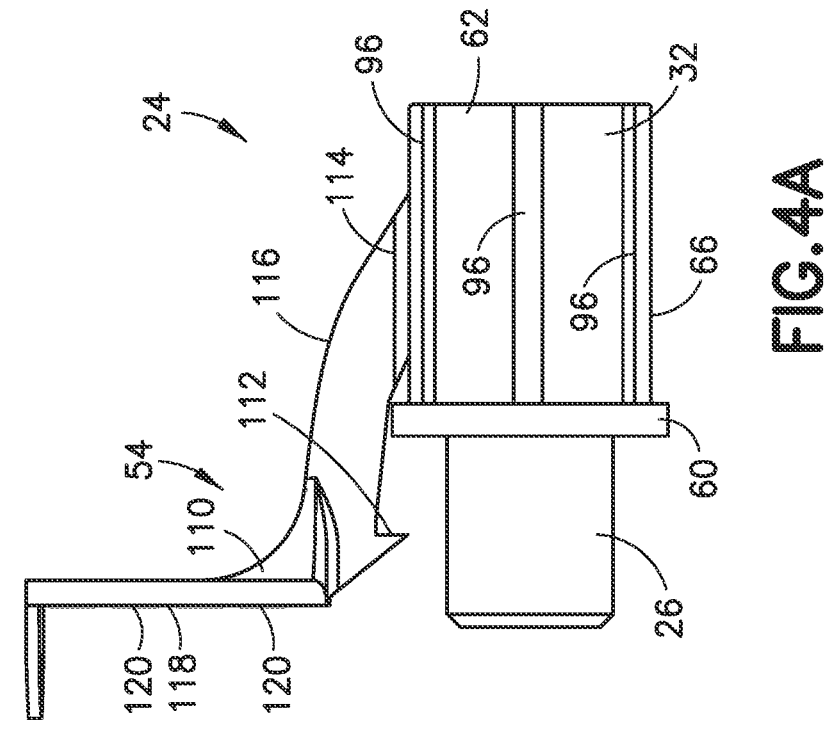
FIG. 4A is a front view of the tip cap of FIG. 1A, according to an aspect of the present disclosure.

With reference to FIGS. 2A-2C, as well as FIGS. 4A and 4B, the syringe 10 further comprises the tip cap 24 connected to the distal end 16 of the barrel 12. The tip cap 24 can be a single molded part, such as a part formed by injection molding. In other examples, the tip cap 24 can be formed from multiple parts connected together by common assembly techniques, such as ultrasonic welding. The tip cap 24 can be formed from a thermoplastic material, such as such as polyester, polycarbonate, polypropylene, polyethylene, polyethylene terephthalate, acrylonitrile butadiene styrene, or other injection moldable or formable resin materials, as are known in the art.

As previously described, the tip cap 24 comprises the connector 26 configured to receive the distal tip 18 of the barrel 12 forming the friction engagement with the distal tip 18, the cap shield 32 connected to and extending about the connector 26, and the release tab 54 extending proximally from the cap shield 32 that secures the tip cap 24 to the barrel 12.

As previously described, the connector 26 is sized to receive the distal tip 18 of the syringe barrel 12. For example, the connector 26 can define a frusto-conical cavity sized to receive the distal tip 18 of the barrel 12. More specifically, in some examples, the connector 26 of the tip cap 24 can shaped as a female needless connector or female luer connector sized to receive the distal tip 18 of the barrel 12. Further, as previously described, the connector 26 can be tapered, such that an inner diameter of a proximal portion of the connector 26 is wider than an inner diameter of a distal portion of the connector 26.

Unlike with some conventional syringe caps, the tip cap 24 of the present disclosure does not engage threads 86 on the inner surface 84 of the distal shield 74 of the barrel 12. Instead, the tip cap 24 is connected to the distal end 16 of the barrel 12 by the combination of the friction engagement between the distal tip 18 of the barrel 12 and the connector 26 of the tip cap 24 and an interference engagement between the catch 112 of the release tab 54 and the collar 64 of the barrel 12. Accordingly, unlike in other cap examples, the outer surface of the connector 26 of the tip cap 24 may not include threads.

In some examples, the cap shield 32 of the tip cap 24 comprises the proximal end 60 comprising a flange connected to and extending radially from the connector 26 of the tip cap 24, the open distal end 62, and a sidewall 66 extending between the proximal end 60 and the distal end 62. The sidewall 66 of the cap shield 32 can further comprise a plurality of axial protrusions 96, such as ribs, ridges, or detents, extending outwardly from an outer surface of the cap shield 32. The protrusions 96, such as axial ridges, can increase rigidity of the cap shield 32 ensuring that the cap shield 32 does not bend or deform during use. The tip cap 24 can further comprise a stem 98 extending distally from a distal end of the connector 26 and at least partially enclosed by the cap shield 32 of the tip cap 24.

With referenced to FIGS. 2A-2C, 4A, and 4B, as previously described, the release tab 54 of the tip cap 24 is configured to provide another point of attachment between the tip cap 24 and the barrel 12 to enhance or secure the friction engagement between the connector 26 of the tip cap 24 and the distal tip 18 of the barrel 12. As previously described, the release tab 54 is configured for single hand release meaning that the practitioner does not need to grasp the syringe 10 with one hand and pull the tip cap 24 away from the syringe 10 with the other hand. Further, the release tab 54 is positioned proximal to other portions of the tip cap 24 and/or proximal to the distal opening 30 of the syringe barrel 12 meaning that the practitioner is unlikely to touch and contaminate the distal opening 30 and/or distal tip 18 of the syringe barrel 12 while removing the tip cap 24 using the release tab 54, which can occur with conventional syringes and caps.

In some examples, the release tab 54 comprises a proximal end 110 comprising the catch 112 for engaging the collar 64 by an interference or snap-fit engagement. As used herein, the catch 112 can refer to a locking structure, such as a hook, groove, curved surface, opening, snap-fit connector, or similar structure or part for engaging a portion of the distal tip 18 and/or barrel 12. In particular, the catch 112 can be configured to grasp and/or press against the collar 64 preventing or restricting axial movement of the tip cap 24 relative to the barrel 12 until the catch 112 is disengaged from the collar 64. The release tab 54 further comprises a distal end 114 pivotally connected to the cap shield 32 of the tip cap 24 at a pivot point and a beam 116 extending between the proximal end 110 and the distal end 114. The beam 116 is configured to move about the pivot point, as shown by arrow A1 in FIG. 2A, from an engaged position (shown for example in FIG. 2A) to a disengaged position, which releases the catch 112 from the collar 64. In some examples, the beam 116 can comprise a living hinged or biased member that is biased to the engaged position. In such examples, the beam 116 causes the catch 112 to snap towards the collar 64, thereby securing the tip cap 24 to the barrel 12. In order to release the release tab 54 from the barrel 12, the practitioner applies sufficient force to the beam 116 to overcome the biasing force of the beam 116 or hinge, which causes the beam 116 to pivot about the pivot point moving the catch 112 away from the collar 64.

In some examples, the proximal end 110 of the release tab 54 comprises a push surface 118 or push plate positioned transverse or substantially transverse to a longitudinal axis X1 (shown in FIGS. 2A-2C) of the connector 26 and to a longitudinal axis X1 of the cap shield 32 of the tip cap 24. As used herein, a surface is transverse or orthogonal to an axis when a line passing over the surface is at a 90 degree angle relative to the axis. A surface is "substantially transverse" to an axis when it is within 10% of being transverse (e.g., angled by about 81 degrees to about 99 degrees relative to the axis X1).

The push surface 118 or push plate can be a flat member comprising an area sized for the practitioner to press against with, for example, one finger, one thumb, or two fingers. In some examples, as shown in FIG. 4B, the push surface 118 can include raised protrusions 120 over the push surface 118 to make the push surface 118 easier to press against and/or to prevent the practitioner's finger(s) or thumb from sliding off the push surface 118 while attempting to release the release tab 54 from the barrel 12. The push surface 118 can be configured such that pressing on the push surface (in a direction of arrow F1 in FIG. 2A) causes the beam 116 to pivot about the distal end 114 of the release tab 54, which releases the catch 112 from the barrel 12. Once the release tab 54 is released, continuing to press against the push surface 118 applies an axial force to the tip cap 24. When the applied axial force overcomes the friction engagement between the connector 26 of the tip cap 24 and the distal tip 18 of the barrel 12, the tip cap 24 slides away from the distal tip 18 of the barrel 12 in a direction of arrow A2 (in FIG. 2B), which releases the tip cap 24 from the barrel 12. Once the practitioner stops applying force to the push surface 118, the release tab 54 moves back to a biased position, as shown by arrow A3 (in FIG. 2B).

Method of Expelling Fluid from a Syringe with a Tip Cap

Figure 5:
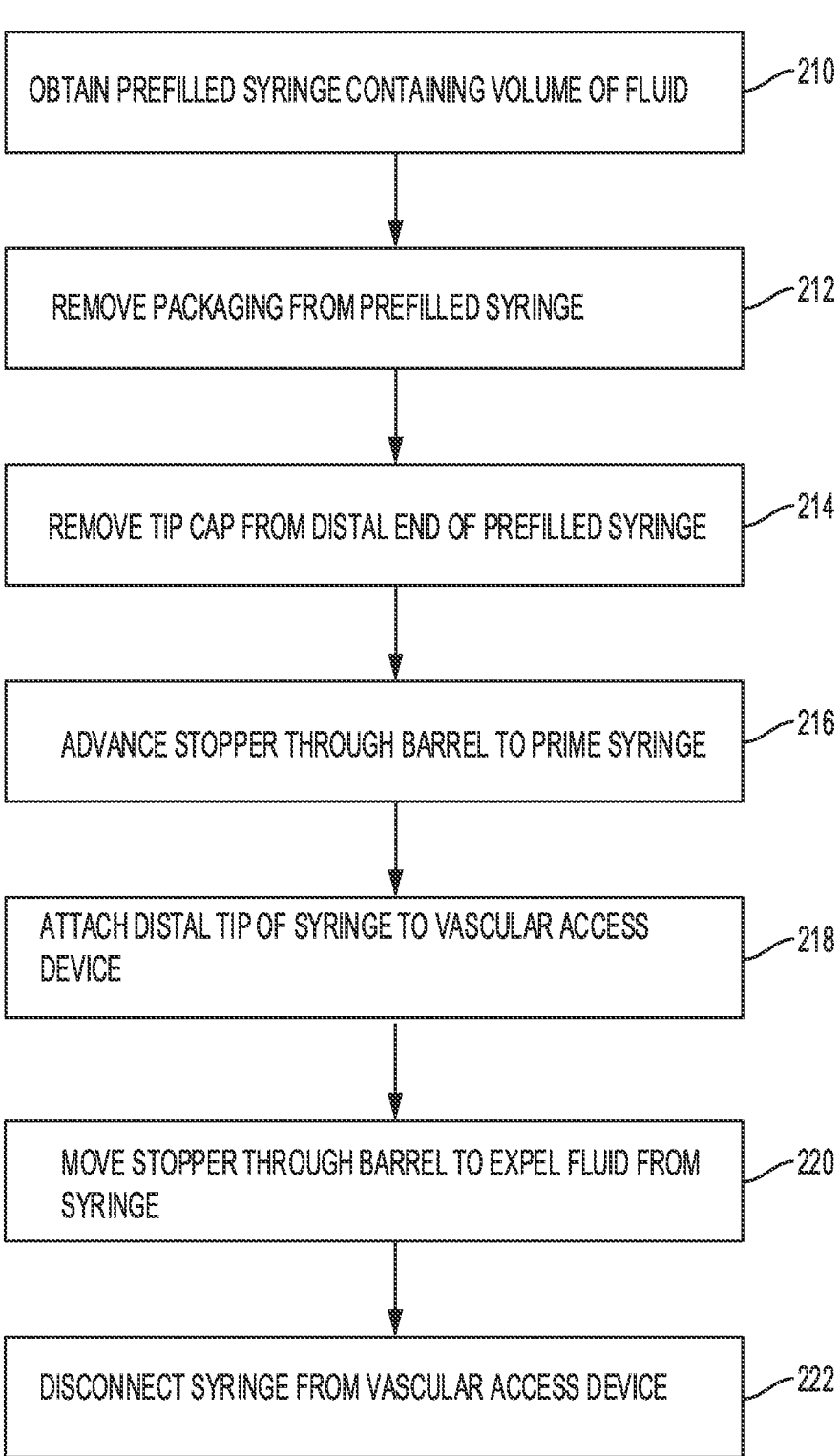
FIG. 5 is a flow chart showing steps for using a prefilled syringe and tip cap for flushing or fluid delivery, according to an aspect of the present disclosure.

A flow chart illustrating steps for using the syringe 10 to expel fluid to a VAD is shown in FIG. 5. As shown in FIG. 5, at step 210, a practitioner initially obtains a prefilled syringe 10, in which the interior of the syringe barrel 12 is filled with a predetermined volume of the medical fluid F. For example, the prefilled syringe 10 can contain about 1 mL to about 50 mL or, preferably, about 5 mL to about 20 mL of the medical fluid F. The tip cap 24 of the prefilled syringe 10 is initially attached to the distal tip 18 of the barrel 12 to ensure that the medical fluid F remains in the interior of the barrel 12 preventing contamination of the fluid and/or fluid leaks. In this initial or prefilled position, the stopper 38 is positioned proximate to the proximal end 14 of the barrel 12 and the plunger rod 40 extends proximally from the stopper 38 and through the proximal end 14 of the barrel 12.

At step 212, the practitioner prepares the syringe 10 for use by, for example, removing any packaging from the syringe 10 and removing a plunger cap, if present, that holds the plunger rod 40 in place.

At step 214, when ready to perform a flush or injection procedure, the practitioner removes the tip cap 24 from the distal tip 18 of the barrel 12. To remove the tip cap 24, the practitioner presses on the push surface 118 at the proximal end 110 of the release tab 54 applying the force F1 (shown in FIG. 2A). The applied force F1 causes the beam 116 to pivot about the distal end 114 of the release tab 54, causing the catch 112 to disengage from the collar 64. Once the catch 112 is disengaged from the collar 64, the practitioner continues to apply pressure to the push surface 118 (as shown by arrow F2 in FIG. 2B). The force F2 overcomes the friction engagement between the distal tip 18 of the barrel 12 and the inner surface 56 of the connector 26 causing the tip cap 24 to slide away from the distal tip 18, as shown by arrow A2 in FIG. 2B. Once the tip cap 24 is removed from the distal tip 18, it can hang in a position proximate to the distal end 16 of the barrel 12 supported by the tether 68. For example, once the tip cap 24 is removed from the distal tip 18, it can swing in a downward direction (shown by arrow A4 in FIG. 2C) remaining proximate to the distal end 16 of the barrel 12.

At step 216, the practitioner next advances the stopper 38 through the barrel 12 by a small amount to remove air from the interior of the syringe barrel 12 by, for example, pressing on the thumb plate 52 of the plunger rod 40 while grasping the finger flange 36 of the barrel 12 between, for example, a ring finger and an index fingers. At step 218, once any air is removed from the interior of the syringe barrel 12, the practitioner next attaches the distal tip 18 of the barrel 12 to the VAD. For example, the practitioner may insert the distal tip 18 of the barrel 12 into a corresponding port or valve of the VAD, in particular into a port or valve of a female needleless connector or female luer connector.

At step 220, once the distal tip 18 is attached to the VAD, the practitioner can move the stopper 38 in the distal direction (shown by arrow D in FIG. 1A) through the interior of the syringe barrel 12 using the plunger rod 40 to expel the medical fluid F from the syringe barrel 12 and through the channel 28 of the distal tip 18. For example, as previously described, the practitioner may press the thumb press plate 52 of the plunger rod 40 with the thumb while grasping the finger flange 36 of the syringe barrel 12 to move the plunger rod 40 in the distal direction (shown by arrow D in FIG. 1A), which causes the stopper 38 to move distally through the syringe barrel 12 to force the medical fluid F from the syringe barrel 12. The practitioner continues to move the stopper 38 distally through the barrel 12 until all or substantially all of the medical fluid F is expelled from the barrel 12 through the channel 28 of the distal tip 18 to the VAD.

At step 222, after the medical fluid F is expelled from the syringe barrel 12, the syringe 10 can be disconnected from the VAD by, for example, rotating the syringe 10 to release the threads 86 of the distal shield 74 from corresponding threads of the female connector and/or by pulling the syringe 10 away from the female connector of the VAD.

As previously described, the prefilled syringe 10 of the present disclosure can be filled with a flush solution and used for performing a primary or pre-flush of the patient line of a VAD. In that case, after the flush solution is expelled from the syringe 10, the syringe 10 can be disconnected from the female connector and another syringe containing another medical fluid, such as a therapeutic agent, can be connected to the female connector for providing the therapeutic agent to the patient. In other examples, the prefilled syringe 10 of the present disclosure can contain a dose of the therapeutic agent to be delivered to the patient through the VAD. In that case, the syringe 10 can be attached to the female connector after flushing in order to provide the therapeutic agent to the patient. In other examples, the prefilled syringe 10 of the present disclosure can contain the flush solution and can be used for a post-flush action. For example, the prefilled syringe 10 can be connected to the VAD after the therapeutic agent is delivered to the patient through the VAD. The flush solution can be expelled from the prefilled syringe 10 through the VAD to flush any remaining therapeutic agent in the VAD to the patient in order to ensure that a full dose of the therapeutic agent is provided to the patient. The post-flush procedure can also ensure that the patient line is clean by removing any debris or other contaminants from the patent line.

Assembly Method for a Syringe and Tip Cap

Figure 3A:
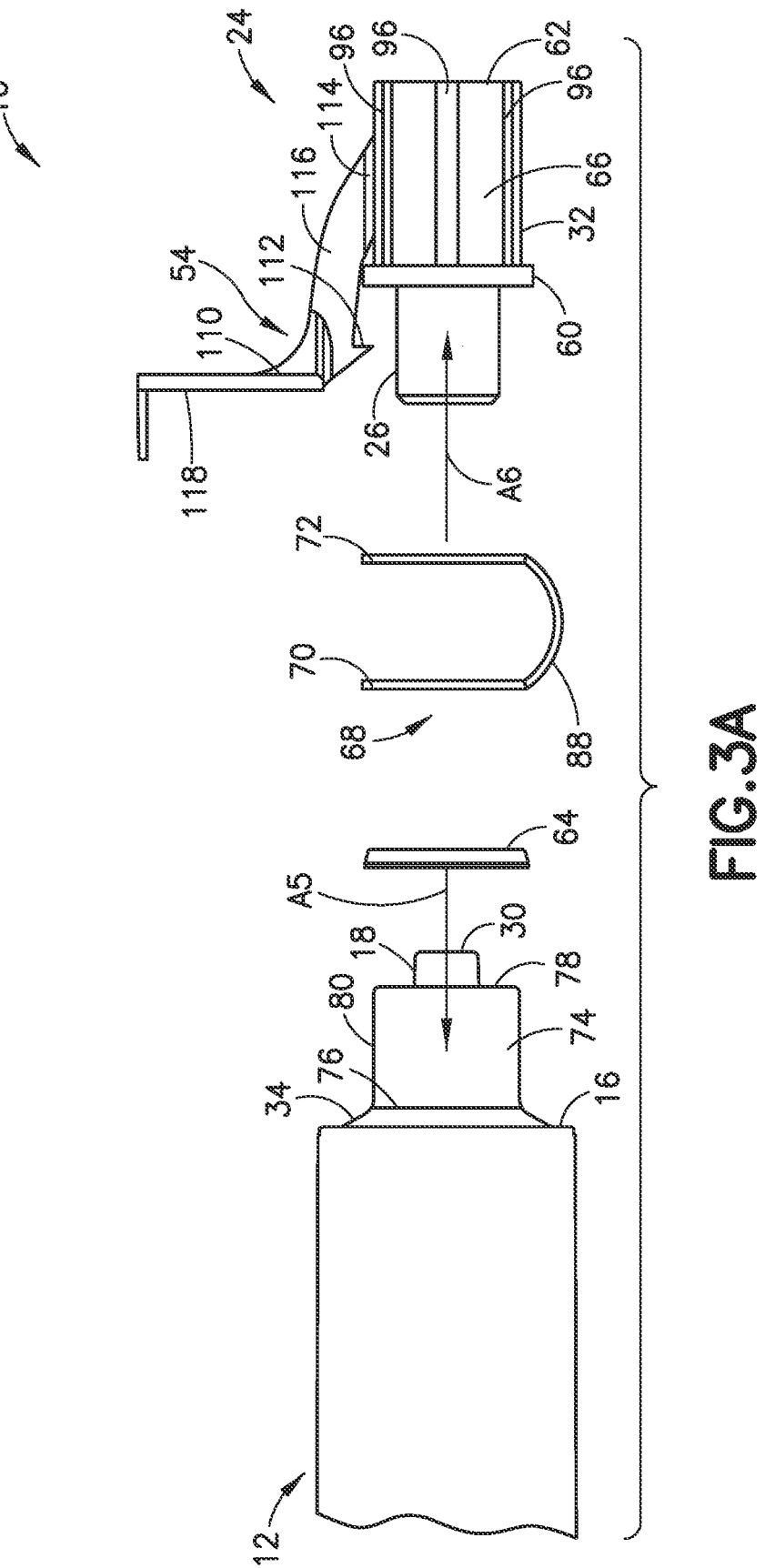
FIGS. 3A-3C are cross-sectional views of the tip cap and syringe of FIG. 1A showing steps for assembling the syringe, according to aspects of the present disclosure.
Figures 3B, 3C:
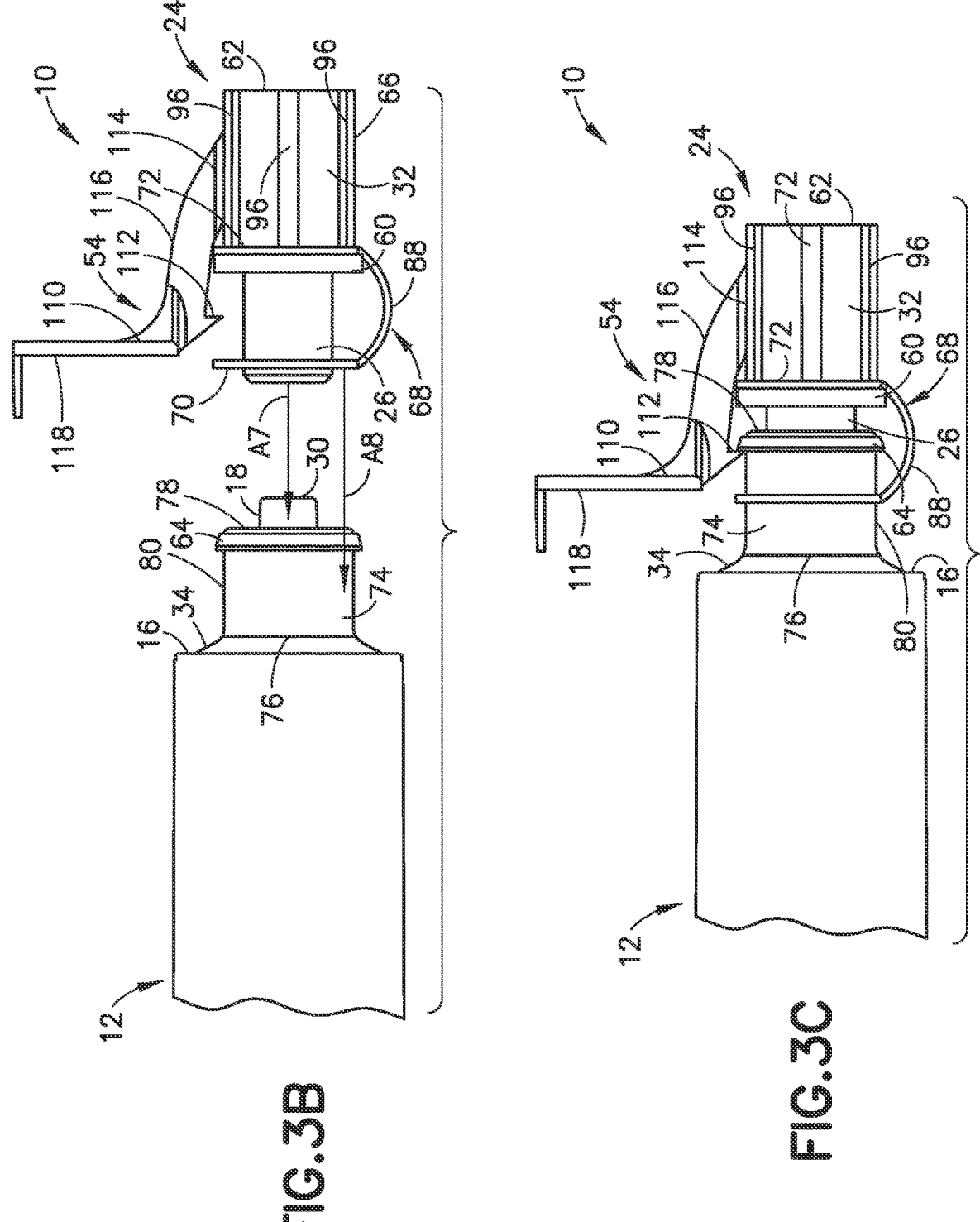
Figure 6:
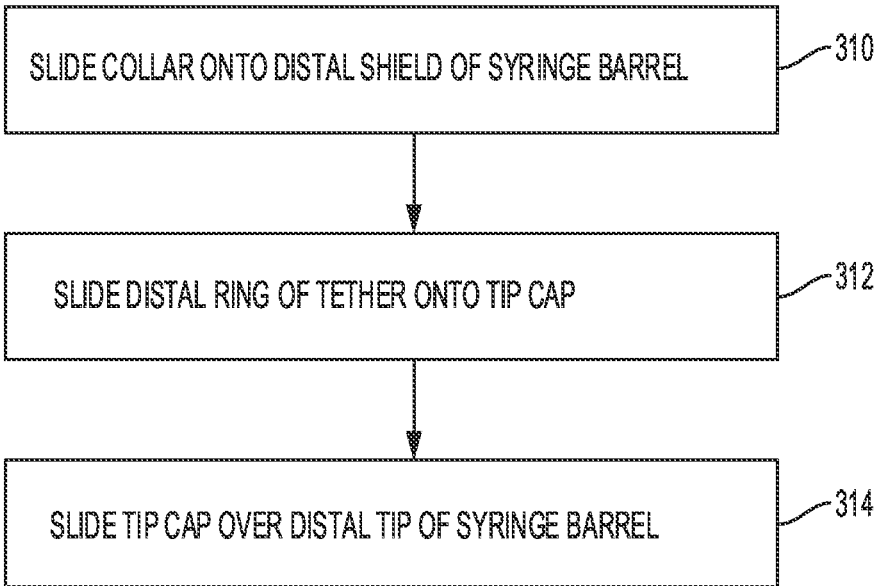
FIG. 6 is a flow chart showing steps for assembly of a syringe and tip cap, according to an aspect of the present disclosure.

FIG. 6 is a flow chart showing a method for assembling the syringe 10 and for attaching the tip cap 24 to the syringe 10. FIGS. 3A-3C show the syringe 10 at different assembly stages. Specifically, FIG. 3A shows parts of the syringe 10 and tip cap 24 prior to assembly. FIG. 3B shows the syringe 10 partially assembled. FIG. 3C shows the syringe 10 fully assembled with the tip cap 24 attached to the syringe 10. As previously described, the tip cap 24 can be attached to a conventional prefilled syringe including the male luer tip or connector. In other examples, the tip cap 24 can be attached to a specially molded or manufactured syringe including integral components (e.g., protrusions, rings, collars, or anchors) on the distal tip 18 of the barrel 12 for mounting the tip cap 24 to the barrel 12.

At step 310, the assembly method comprises moving the collar 64 in a direction of arrow A5 (shown in FIG. 3A) to slide the collar 64 onto the distal shield 74 of the barrel 12. As previously described, the collar 64 can be a rigid plastic ring that slides onto the distal shield 74. The collar 64 can be held in place on the shield 74 due to a friction engagement between an inner surface of the collar 64 and an outer surface of the shield 74.

At step 312, the method further comprises moving the distal ring 72 of the tether 68 in a direction of arrow A6 (shown in FIG. 3A) to slide the distal ring 72 onto the cap shield 32 of the tip cap 24. For example, the distal ring 72 can slide over the flange on the proximal end 60 of the cap shield 32 and can be positioned against an outer surface of the sidewall 66 of the cap shield 32.

At step 314, after the collar 64 and distal ring 72 are in place, the tip cap 24 is moved towards the distal tip 18 of the barrel 12 (as shown by arrow A7 in FIG. 3B) causing the connector 26 of the tip cap 24 to slide into the distal shield 74 and over the distal tip 18 of the barrel 12. As previously described, the connector 26 forms a friction engagement with the distal tip 18, for retaining the tip cap 24 on the distal tip 18. Also, moving the tip cap 24 towards the distal tip 18 causes the release tab 54 to move towards the collar 64. Specifically, the catch 112 of the release tab 54 contacts or snaps against a proximal side of the collar 64 (as shown in FIG. 3C), thereby forming an interference engagement between the collar 64 and the catch 112, which enhances the attachment between the tip cap 24 and the barrel 12. Moving the tip cap 24 towards the barrel 12 also causes the proximal ring 70 of the tether 68 to move (as shown by arrow A8 in FIG. 3B) proximally over the collar 64 sliding along the distal shield 74 of the barrel 12.

The syringe 10 and tip cap 24 are shown in an assembled configuration in FIG. 3C. As shown in FIG. 3C, the proximal ring 70 of the tether 68 and the collar 64 are both positioned over the distal shield 74 of the barrel 12. Further, the catch 112 contacts the proximal side of the collar 64 forming the interference engagement between the release tab 54 and the collar 64. Also, the connector 26 of the tip cap 24 is engaged to (i.e. by a friction engagement) and positioned over the distal tip 18 of the barrel 12 preventing contamination of the distal tip 18 and also preventing fluid contained in the barrel 12 from leaking through the distal opening 30 of the distal tip 18. In addition, the distal ring 72 of the tether 68 is attached to the cap shield 32 at a position distal to the flange on the proximal end 60 of the cap shield 32. Once the syringe 10 in the assemble position (as shown in FIG. 3C), it can be used as previously described and as shown in the flow chart of FIG. 5.

While examples of the syringe 10 comprising the tip cap 24 and methods of the present disclosure are shown in the accompanying figures and described hereinabove in detail, other examples will be apparent to, and readily made by, those skilled in the art without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A syringe comprising:
a barrel comprising a proximal end, a distal end comprising a distal tip defining a channel, and a sidewall extending between the proximal end and the distal end, wherein the distal end of the barrel further comprises a distal shield at least partially enclosing the distal tip of the barrel, a tether connecting the barrel to the tip cap so that the tip cap can hang from the barrel when the connector of the tip cap is removed from the distal tip of the barrel, and wherein the tether comprises a proximal ring positioned about the distal shield of the barrel, a distal ring connected about the cap shield of the tip cap, and a connecting member extending between the proximal ring and the distal ring; and
a tip cap removably connected to the distal tip of the barrel restricting fluid flow from the channel, the tip cap comprising: a connector configured to receive the distal tip of the barrel forming a friction engagement with the distal tip, a cap shield connected to and extending about the connector, and a release tab extending proximally from the cap shield that secures the tip cap to the barrel.

2. The syringe of claim 1, further comprising a tether connecting the barrel to the tip cap so that the tip cap hangs from the barrel when the connector of the tip cap is removed from the distal tip of the barrel.

3. The syringe of claim 1, further comprising a collar around the distal shield of the barrel, and wherein the release tab comprises a catch removably engaged to the collar.

4. The syringe of claim 3, wherein the collar is engaged about an outer surface of the distal shield of the barrel.

5. The syringe of claim 1, wherein the proximal ring, the distal ring, and the connecting member of the tether comprise a flexible elastomeric material.

6. The syringe of claim 1, wherein the connector of the tip cap defines a frusto-conical cavity sized to receive the distal tip of the barrel.

7. The syringe of claim 1, wherein the connector of the tip cap comprises a female luer connector sized to receive the distal tip of the barrel.

8. The syringe of claim 1, wherein an outer surface of the connector of the tip cap does not include threads.

9. The system of claim 1, wherein the cap shield of the tip cap comprises a proximal end comprising a flange connected to and extending radially from the connector of the tip cap, an open distal end, and a sidewall extending between the proximal end and the distal end.

10. The syringe of claim 9, wherein the sidewall of the cap shield comprises a plurality of axial ridges extending outwardly from an outer surface of the cap shield.

11. The syringe of claim 1, wherein the tip cap further comprises a stem extending distally from a distal end of the connector and enclosed by the cap shield of the tip cap.

12. The syringe of claim 1, wherein the release tab comprises a proximal end comprising a catch for engaging the barrel, a distal end pivotally connected to the cap shield of the tip cap, and a beam extending between the proximal end and the distal end.

13. The syringe of claim 12, wherein the proximal end of the release tab further comprises a push surface that is transverse or substantially transverse to a longitudinal axis of the connector of the tip cap and to a longitudinal axis of the cap shield of the tip cap.

14. The syringe of claim 13, wherein pressing on the push surface causes the beam to pivot about the distal end of the release tab, which releases the catch from the barrel, and wherein continuing to press against the push surface overcomes the friction engagement between the connector of the tip cap and the distal tip of the barrel, which disconnects the tip cap from the distal tip of the barrel.

15. The syringe of claim 1, wherein the tip cap is an integrally molded part comprising at least one of polyester, polycarbonate, polypropylene, polyethylene, polyethylene terephthalate, or acrylonitrile butadiene styrene.

16. A prefilled flushing syringe, comprising:
the syringe of claim 1; and
a predetermined volume of a fluid disposed in the barrel of the prefilled syringe,
wherein the distal tip of the barrel is received within the connector of the tip cap, thereby preventing the fluid in the barrel from passing through the channel to a distal opening of the barrel, and
wherein the release tab of the tip cap is engaged to a portion of the barrel, thereby securing the tip cap to the barrel.

17. A method for expulsion of fluid from the syringe of claim 1, the method comprising:
removing the tip cap from the distal tip of the syringe barrel;
attaching the distal tip of the syringe barrel to a vascular access device; and
moving a plunger inserted in the barrel through the barrel to expel the fluid from the barrel and through the channel of the distal tip of the barrel to the vascular access device.

18. A method for assembly of the syringe of claim 1, the method comprising:
attaching a collar over a distal shield of the syringe barrel;
attaching a distal ring of a tether onto the tip cap; and
moving the connector of the tip cap over the distal tip of the barrel, thereby forming an assembled syringe.

\* \* \* \* \*